(12) United States Patent
Sulley et al.

(10) Patent No.: US 10,835,598 B2
(45) Date of Patent: Nov. 17, 2020

(54) PROPHYLACTIC PROTECTION AGAINST VIRAL INFECTIONS, PARTICULARLY HIV

(71) Applicant: Tamir Biotechnology, Inc., Short Hills, NJ (US)

(72) Inventors: Jamie Sulley, La Jolla, CA (US); Luis Squiquera, Buenos Aires (AR); David Sidransky, Pikesville, MD (US); Tom Hodge, Athens, GA (US)

(73) Assignee: ORGENESIS INC., Germantown, MD (US)

( * ) Notice: Subject to any disclaimer, the term of this patent is extended or adjusted under 35 U.S.C. 154(b) by 297 days.

(21) Appl. No.: 15/582,133

(22) Filed: Apr. 28, 2017

(65) Prior Publication Data

US 2017/0296647 A1    Oct. 19, 2017

Related U.S. Application Data

(63) Continuation-in-part of application No. 14/793,920, filed on Jul. 8, 2015, now Pat. No. 9,642,794, which is a continuation-in-part of application No. 14/462,520, filed on Aug. 18, 2014, now abandoned.
(Continued)

(51) Int. Cl.
*A61K 38/54* (2006.01)
*A61K 39/21* (2006.01)
(Continued)

(52) U.S. Cl.
CPC .......... *A61K 39/21* (2013.01); *A61K 9/0014* (2013.01); *A61K 9/0034* (2013.01);
(Continued)

(58) Field of Classification Search
None
See application file for complete search history.

(56) References Cited

U.S. PATENT DOCUMENTS 4,882,421 A   11/1989  Shogen et al.
5,559,212 A    9/1996  Ardelt
(Continued)

FOREIGN PATENT DOCUMENTS

WO   WO 1996/039428 A1   12/1996
WO   WO 1997/031116 A2    8/1997
(Continued)

OTHER PUBLICATIONS

Gray et al., "Approaches to Preventative and Therapeutic HIV vaccines," Curr Opin Virol 17: 104-109 (Year: 2016).*
(Continued)

*Primary Examiner* — M Franco G Salvoza
(74) *Attorney, Agent, or Firm* — Mark S. Cohen; Pearl Cohen Zedek Latzer Baratz LLP

(57) ABSTRACT

An experiment has shown that ranpirnase is a microbicide. It is believed that topical application of a topical pharmaceutical composition consisting essentially of a prophylactically effective concentration of an enzymatically-active ribonuclease (e.g. ranpirnase) and a viscous vehicle that does not unacceptably interfere with the enzymatic activity (e.g. K-Y® Brand Jelly) will prophylactically protect an individual from a sexually-transmitted viral infection, particularly HIV. It is also believed that e.g. ranpirnase can be delivered to tissues of an individual who is to be prophylactically protected against viral infections by transfecting ranpirnase DNA into human microbiota and exposing the individual to the thus-modified human microbiota. It is also believed that ranpirnase can be delivered to a woman who is to be prophylactically protected against a sexually-transmitted viral infection by use of an intravaginal ring that has been impregnated with ranpirnase.

2 Claims, 2 Drawing Sheets

Specification includes a Sequence Listing.

Related U.S. Application Data

(60) Provisional application No. 62/367,050, filed on Jul. 26, 2016.

(51) Int. Cl.

| | | |
|---|---|---|
| *C07K 14/16* | (2006.01) | |
| *C07K 7/08* | (2006.01) | |
| *C12N 15/86* | (2006.01) | |
| *A61K 38/46* | (2006.01) | |
| *A61K 9/00* | (2006.01) | |
| *A61K 35/744* | (2015.01) | |
| *A61K 35/747* | (2015.01) | |
| *C12N 9/22* | (2006.01) | |
| *A61K 38/00* | (2006.01) | |
| *A61K 39/00* | (2006.01) | |
| *A61K 48/00* | (2006.01) | |

(52) U.S. Cl.
CPC .......... *A61K 35/744* (2013.01); *A61K 35/747* (2013.01); *A61K 38/465* (2013.01); *C07K 7/08* (2013.01); *C07K 14/16* (2013.01); *C12N 9/22* (2013.01); *C12N 15/86* (2013.01); *C12Y 301/27005* (2013.01); *A61K 38/00* (2013.01); *A61K 39/00* (2013.01); *A61K 48/00* (2013.01); *A61K 2039/525* (2013.01); *A61K 2039/53* (2013.01); *C12N 2740/16043* (2013.01); *C12N 2740/16334* (2013.01); *C12Y 301/27* (2013.01)

(56) References Cited

U.S. PATENT DOCUMENTS

| | | | |
|---|---|---|---|
| 5,728,805 | A | 3/1998 | Ardelt |
| 5,955,073 | A | 9/1999 | Rybak et al. |
| 6,159,491 | A * | 12/2000 | Durrani ............... A61K 9/0034 424/430 |
| 6,175,003 | B1 | 1/2001 | Saxena |
| 6,239,257 | B1 | 5/2001 | Ardelt |
| 6,423,515 | B1 | 7/2002 | Saxena |
| 7,229,824 | B2 | 6/2007 | Saxena |
| 7,442,535 | B2 | 10/2008 | Saxena |
| 7,442,536 | B2 | 10/2008 | Saxena |
| 7,473,542 | B2 | 1/2009 | Saxena |
| 7,556,951 | B2 | 7/2009 | Saxena |
| 7,556,952 | B2 | 7/2009 | Saxena |
| 7,556,953 | B2 | 7/2009 | Saxena |
| 7,572,882 | B2 | 8/2009 | Sette et al. |
| 7,585,654 | B2 | 9/2009 | Saxena |
| 7,585,655 | B2 | 9/2009 | Saxena |
| 7,763,449 | B2 | 7/2010 | Saxena |
| 8,518,399 | B2 | 8/2013 | Saxena et al. |
| 8,663,964 | B2 | 3/2014 | Saxena et al. |
| 8,808,690 | B2 | 8/2014 | Saxena et al. |
| 9,642,794 | B2 | 5/2017 | Sulley et al. |
| 9,919,034 | B2 | 3/2018 | Hodge |
| 10,293,032 | B2 | 5/2019 | Squiquera et al. |
| 2003/0099629 | A1 | 5/2003 | Goldenberg et al. |
| 2004/0072910 | A1 | 4/2004 | Porat |
| 2005/0014161 | A1 | 1/2005 | Saxena |
| 2007/0231890 | A1 | 10/2007 | Saxena |
| 2007/0231891 | A1 | 10/2007 | Saxena |
| 2007/0232543 | A1 | 10/2007 | Saxena |
| 2007/0232544 | A1 | 10/2007 | Saxena |
| 2007/0238861 | A1 | 10/2007 | Saxena |
| 2007/0243605 | A1 | 10/2007 | Saxena |
| 2007/0243606 | A1 | 10/2007 | Saxena |
| 2008/0033151 | A1 | 2/2008 | Saxena |
| 2008/0161324 | A1 | 7/2008 | Johansen et al. |
| 2009/0081759 | A1 | 3/2009 | Saxena |
| 2009/0081776 | A1 | 3/2009 | Saxena |
| 2009/0081777 | A1 | 3/2009 | Saxena |
| 2009/0081778 | A1 | 3/2009 | Saxena |
| 2009/0099348 | A1 | 4/2009 | Saxena |
| 2009/0111175 | A1 | 4/2009 | Saxena |
| 2009/0202513 | A1 | 8/2009 | Ramon-nino et al. |
| 2009/0246214 | A1 | 10/2009 | Goldenberg et al. |
| 2010/0291657 | A1 | 11/2010 | Saxena |
| 2010/0304463 | A1 | 12/2010 | Saxena |
| 2010/0317082 | A1 | 12/2010 | Saxena |
| 2011/0274704 | A1 | 11/2011 | Chang et al. |
| 2012/0121569 | A1 | 5/2012 | Saxena et al. |
| 2012/0149085 | A1 | 6/2012 | Goldenberg et al. |
| 2012/0260922 | A1 | 10/2012 | Gomez-acebo et al. |
| 2013/0022589 | A1 | 1/2013 | Saxena et al. |
| 2014/0030246 | A1 | 1/2014 | Saxena et al. |
| 2014/0037610 | A1 | 2/2014 | Saxena et al. |
| 2014/0128396 | A1 | 5/2014 | Schadt et al. |
| 2015/0010524 | A1 | 1/2015 | Jain |
| 2015/0376584 | A1 | 12/2015 | Hodge |
| 2016/0045431 | A1 | 2/2016 | Sulley et al. |
| 2016/0045574 | A1 | 2/2016 | Sulley et al. |
| 2016/0361392 | A1 | 12/2016 | Squiquers et al. |
| 2017/0157219 | A1 | 6/2017 | Hodge |
| 2019/0216904 | A1 | 7/2019 | Squiquera et al. |

FOREIGN PATENT DOCUMENTS

| | | |
|---|---|---|
| WO | WO 1997/038112 A1 | 10/1997 |
| WO | WO 2000/040608 A1 | 7/2000 |
| WO | WO 2001/018214 A1 | 3/2001 |
| WO | WO 2004/061120 A2 | 7/2004 |
| WO | WO 2005/017100 A2 | 2/2005 |
| WO | WO 2005/080586 A1 | 9/2005 |
| WO | WO 2013/039857 A1 | 3/2013 |
| WO | WO 2013/089835 A1 | 6/2013 |
| WO | WO 2016/028634 A1 | 8/2015 |
| WO | WO 2015/148768 A2 | 10/2015 |
| WO | WO 2016/205109 A1 | 12/2016 |
| WO | WO 2017/142807 A1 | 8/2017 |
| WO | WO 2018/022774 A1 | 2/2018 |

OTHER PUBLICATIONS

Markel et al., "Sexually transmitted diseases," Prim Care 40(3): 557-87 (Year: 2013).*
FDA CDER, "Guidance for Industry: Vaginal Microbicides: Development for the Prevention of HIV Infection," Office of Communications, FDA, U.S.Department of Health and Human Services, available at https://www.fda.gov/media/85288/download (Year: 2014).*
PCT/US2016/037174, International Preliminary Report on Patentability, dated Dec. 19, 2017, 9 pages.
PCT/US2017/043984, International Search Report and Written Opinion, dated Oct. 10, 2017, 15 pages.
Langston, "Herpes Simplex Virus in the Eye", Digital Journal of Ophthalmology, Oct. 15, 2002, 3 pages.
PCT/US1999/030799, International Search Report and Written Opinion dated May 30, 2000, 7 pages.
PCT/US2000/023426, International Search Report dated Nov. 27, 2000, 3 pages.
PCT/US2004/014844, International Search Report and Written Opinion, dated May 10, 2006, 8 pages.
PCT/US2004/014844, International Preliminary Report on Patentability, dated Feb. 15, 2007, 5 pages.
PCT/US2015/022670, International Search Report and Written Opinion, dated Nov. 18, 2015, 29 pages.
PCT/US2015/022670, International Preliminary Report on Patentability, dated Oct. 4, 2016, 21 pages.
PCT/US2015/045272, International Search Report and Written Opinion, dated Dec. 1, 2015, 9 pages.
PCT/US2015/045272, International Preliminary Report on Patentability, dated Feb. 21, 2017, 6 pages.
PCT/US2016/037174, International Search Report and Written Opinion, dated Oct. 12, 2016, 14 pages.
"Anti Viral Status in Quarterly Report for Tamir Biotechnology." Alfacell Corporation, ACEL—InvestorVillage, published Aug. 15, 2011 [retrieved on Feb. 8, 2017]. Retrieved from the internet, 2 pages. <URL:http://www.investorvillage.com/mbthread.asp?mb=470&tid=10843482&showall=1>.

(56) References Cited

OTHER PUBLICATIONS

"Tamir Reports Positive Effect Against SARS Virus." Tamir Biotechnology, Inc., published on Oct. 21, 2010 [retrieved on Feb. 8, 2017]. Retrieved from the internet, 2 pages. <URL:http://globenewswire.com/news-release/2010/07/21/425595/197044/en/Tamir-Reports-Positive-Effect-Against-SARS-Virus.html>.

"Tamir's Compounds Show Remarkable Results Against Dengue Virus", Tamir Biotechnology, Inc., published Jul. 19, 2010 [retrieved on Feb. 8, 2017]. Retrieved from the internet, 3 pages. <URL:http://www.globenewswire.com/news-release/2010/07/19/425341/196757/en/Tamir-s-Compounds-Show-Remarkable-Results-Against-Dengue-Virus.html>.

Adinolfi, B.S., et al., "Full antitumor action of recombinant seminal ribonuclease depends on the removal of its N-terminal methionine." Biochem Biophys Res Commun. (1995); 213(2): 525-532.

Anonymous: "Baltimore classification—Wikipedia, the free encyclopedia", published Mar. 6, 2013 [retrieved on Feb. 13, 2013]. Retrieved from the internet, 5 pages. <URL:https://en.wikipedia.org/w/index.php?title=Baltimore_classification&oldid=542396320>.

Ardelt, W., et al., "Amino acid sequence of an anti-tumor protein from Rana pipiens oocytes and early embryos. Homology to pancreatic ribonucleases." J Biol Chem. (1991); 266(1): 245-251.

Ardelt, W., et al., "Onconase and Amphinase, the Antitumor Ribonucleases from Rana pipiens Oocytes." Curr Pharm Biotechnol. (2008); 9(3): 215-225.

Baltimore, D., "Expression of Animal Virus Genomes", Bacteriological Reviews (1971); 35(3): 235-241.

Boix, E., et al., "Role of the N terminus in RNase A homologues: differences in catalytic activity, ribonuclease inhibitor interaction and cytotoxicity." J Mol Biol. (1996); 257(5): 992-1007.

Branden et al., Introduction to Protein Structure, Garland Publishing Inc., New York, p. 247, 1991, 24 pages.

Bucher, M.H., et al., "Differential effects of short affinity tags on the crystallization of Pyrococcus furiosus maltodextrin-binding protein." Acta Crystallogr D Biol Crystallogr. (2002);58(Pt 3): 392-397. Epub Feb. 21, 2002.

Chao, Q., et al., "Expression and partial characterization of Dolichos biflorus seed lectin in Escherichia coli." Arch Biochem Biophys. (1994); 313(2): 346-350.

Chaudhuri, T.K., et al., "Effect of the extra n-terminal methionine residue on the stability and folding of recombinant α-lactalbumin expressed in Escherichia coli." J Mol Biol. (1999); 285(3): 1179-1194.

Chen, C-Y., et al., "Cloning, sequencing and expression of a cDNA encoding bovine pancreatic deoxyribonuclease I in Escherichia coli: purification and characterization of the recombinant enzyme." Gene (1998); 206(2): 181-184.

Domachowske, J.B. et al., "Eosinophil cationic protein/RNase 3 is another RNase A-family ribonuclease with direct antiviral activity", Nucleic Acids Research (1998); 26(14): 3358-3363.

Durmazlar, K., et al., "Cantharidin treatment for recalcitrant facial flat warts: a preliminary study." J. Dermatol. Treatment (2009); 20(2): 114-119.

Dyer and Rosenberg, "The RNase a superfamily: generation of diversity and innate host defense." Mol Divers. (2006); 10(4): 585-597.

Fonda, I., et al., "Attachment of histidine tags to recombinant tumor necrosis factor-alpha drastically changes its properties." ScientificWorldJournal (2002); 2: 1312-1325.

Geurrero, S.A., et al., "His-tagged tryparedoxin peroxidase of Trypanosoma cruzi as a tool for drug screening." Appl Microbiol Biotechnol. (2000); 53(4): 410-414.

Goda, S., et al., "Effect of extra N-terminal residues on the stability and folding of human lysozyme expressed in Pichia pastoris." Protein Engineering (2000); 13(4): 299-307.

Gupta, P.K., et al., "Role of N-Terminal Amino Acids in the Potency of Anthrax Lethal Factor." PLoS One (2008); 3(9): e3130.

Hariri, S., et al., "Human Papillomavirus." Centers for Disease Control Vpd Surveillance Manual, 5th edition, Chapter 5, pp. 1-11 (2011).

Hirel, P.H., et al., "Extent of N-terminal methionine excision from Escherichia coli proteins is governed by the side-chain length of the penultimate amino acid." PNAS USA (1989); 86(21): 8247-8251.

Ho, S.N., et al., "Site-directed mutagenesis by overlap extension using the polymerase chain reaction." Gene (1989); 77(1): 51-59.

Huang, H-C., et al., "The Rana catesbeiana rcr Gene Encoding a Cytotoxic Ribonuclease. Tissue Distribution, Cloning, Purification, Cytotoxicity, and Active Residues for RNase Activity." J. Biol. Chem. (1998); 273(11): 6395-6401.

Ilinskaya and Mahmud, "Ribonucleases as antiviral agents." Molecular Biology (2014); 48(5): 615-623 (Abstract).

Ishikiwa, N., et al., "Remarkable destabilization of recombinant alpha-lactalbumin by an extraneous N-terminal methionyl residue." Protein Eng. (1998); 11(5): 333-335.

Kamiya, Y., et al., "Amino acid sequence of a lectin from Japanese frog (Rana japonica) eggs." J Biochem. (1990); 108(1): 139-143.

Lehninger, A.L. (1975) Biochemistry, Second Edition, p. 962, 5 pages.

Liao, Y.D., et al., "Removal of N-terminal methionine from recombinant proteins by engineered E. coli methionine aminopeptidase." Protein Sci. (2004); 13(7): 1802-1810.

Lin, J-J. et al., "Characterization of the mechanism of cellular and cell free protein synthesis inhibition by an anti-tumor ribonuclease", Biochemical and Biophysical Research Communications (1994); 204(1): 156-162.

Moore, J.A., et al., "Equivalent Potency and Pharmacokinetics of Recombinant Human Growth Hormones with or without an N-Terminal Methionine." Endocrinology (1988); 122(6): 2920-2926.

Moreau, J.M. et al., "Diminished expression of an antiviral ribonuclease in response to pneumovirus infection in vivo" Antiviral Research (2003); 59(3): 181-191 (Abstract).

Mosimann, S.C., et al., "Comparative molecular modeling and crystallization of P-30 protein: A novel antitumor protein of Rana pipiens oocytes and early embryos." Proteins (1992); 14(3): 392-400.

Notomista, E., et al., "Effective expression and purification of recombinant onconase, an antitumor protein." FEBS Letters (1999); 463(3): 211-215.

Park, K.S., et al., "Biologic and biochemic properties of recombinant platelet factor 4 demonstrate identity with the native protein." Blood (1990); 75: 1290-1295.

Porta, C., et al., "Ranpirnase and its potential for the treatment of unresectable malignant mesothelioma." Biologics (2008); 2(4): 601-609.

Qiao, M. et al., "Onconase downregulates microRNA expression through targeting microRNA precursors", Cell Research (2012); 22(7): 1199-1202.

Saxena, S.K., et al., "Effect of Onconase on Double-stranded RNA In Vitro." Anticancer Research (2009); 29(4): 1067-1072.

Saxena, S.K., et al., "Inhibition of HIV-1 production and selective degradation of viral RNA by an amphibian ribonuclease." J Biol Chem. (1996); 271(34): 20783-20788.

Saxena, S.K., et al., "Onconase® and its Therapeutic Potential." Lab Medicine (2003); 34(5): 380-387.

Seffernick, J.L., et al., "Melamine Deaminase and Atrazine Chlorohydrolase: 98 Percent Identical but Functionally Different." Journal of Bacteriology (2001); 183(8): 2405-2410.

Studier, F.W., et al., "Use of T7 RNA polymerase to direct expression of cloned genes." Methods Enzymol. (1990); 185: 60-89.

Suhasini and Sirdeshmukh, "Transfer RNA cleavages by onconase reveal unusual cleavage sites." J Biol Chem. (2006); 281(18): 12201-12209. Epub Feb. 23, 2006.

Supplementary European Search Report in European application No. EP 04751988.9, completed May 30, 2007 and dated Jun. 6, 2007, 6 pages.

Suzuki, M., et al., "Engineering receptor-mediated cytotoxicity into human ribonucleases by steric blockade of inhibitor interaction." Nat Biotechnol. (1999); 17(3): 265-270.

Takano, K., et al., "Effect of foreign N-terminal residues on the conformational stability of human lysozyme." The FEBS Journal (1999); 266(2): 675-682.

Trimble and Frazer, "Development of therapeutic HPV vaccines." Lancet Oncol. (2009); 10(10): 975-980.

(56) References Cited

OTHER PUBLICATIONS

Turcotte and Raines, "Design and Characterization of an HIV-Specific Ribonuclease Zymogen." AIDS Res Hum Retroviruses (2008); 24(11): 1357-1363.
UniProtKB—Amphinase-2 entry (2007), 5 pages.
Witkowski, A., et al., "Conversion of a β-Ketoacyl Synthase to a Malonyl Decarboxylase by Replacement of the Active-Site Cysteine with Glutamine." Biochemistry, (1999); 38(36): 11643-11650.
Wu and Filutowicz, "Hexahistidine ($His_6$)-tag dependent protein dimerization: a cautionary tale." Acta Biochim Pol. (1999); 46(3): 591-599.
Wu, Y., et al., "A cytotoxic ribonuclease. Study of the mechanism of onconase cytotoxicity." The Journal of Biological Chemistry (1993); 268(14): 10686-10693.

* cited by examiner

Tamir Study- Effectiveness of Ranpirnase in Explant Challenge Model: Cumulative HIV Infection at 14 Days

PROPHYLACTIC PROTECTION AGAINST VIRAL INFECTIONS, PARTICULARLY HIV

CROSS-REFERENCE TO RELATED APPLICATIONS

This application claims priority to U.S. Provisional application No. 62/367,050 filed Jul. 26, 2016. This application is also a continuation-in-part of application Ser. No. 14/793,920, filed Jul. 8, 2015, which is a continuation-in-part of application Ser. No. 14/462,520, filed Aug. 18, 2014. The entire disclosure of these applications are hereby expressly incorporated herein by reference for all purposes.

CROSS-REFERENCE TO SEQUENCE LISTING

The contents of the text file submitted electronically herewith are incorporated herein by reference in their entirety: A computer readable format copy of the Sequence Listing (filename: TAMI_014_02US_SeqList_ST25.txt, date recorded: Apr. 28, 2017, file size 4 kilobytes).

BACKGROUND OF THE INVENTION

The disclosure relates to prophylactic protection against viral infections, and more particularly relates to antiviral prophylactic protection that requires neither injection nor oral administration of a prophylactic agent. In its most immediate sense, the invention relates to use of an enzymatically-active ribonuclease, and particularly use of ranpirnase, to prophylactically protect an individual from viral infections such as human immunodeficiency virus ("HIV").

Sexually transmitted infections, and particularly HIV, pose a significant public health threat. At present, individuals wishing to protect themselves against such infections must rely upon mechanical measures (such as condoms and dental dams) that prevent them from coming into contact with their partner's bodily fluids, which may contain HIV. These measures are non-optimal because some individuals are reluctant to use them. More recently, the use of orally administered antiretrovirals (e.g. tenofovir) has been postulated as pre-exposure prophylactic treatment. While oral prophylaxis is effective, it suffers from significant disadvantages. Oral prophylaxis must be used consistently for a prolonged period and its effectiveness is reduced or even eliminated if the patient is not fully compliant. Other oral medications can adversely affect the efficacy of oral prophylaxis. And, the effectiveness of an orally administered drug can be seriously compromised if a patient suffers from nausea or from diarrhea.

It would be advantageous to provide prophylaxis against sexually transmitted infections, and more particularly against HIV, that did not require the use of mechanical measures such as condoms and dental dams and that did not need to be administered orally or by injection.

DETAILED DESCRIPTION

It is known that ranpirnase is active against HIV. However, an experiment has shown something unexpected, namely, that topically-applied ranpirnase acts as a microbicide, i.e. that ranpirnase can prevent cells from becoming infected with HIV. In this experiment, rectal tissue biopsies taken from HIV-uninfected individuals were incubated in solutions containing a mixture of ranpirnase and HIV. The explanted tissues were then cultured and supernatant was collected at intervals. The supernatant was assayed to quantify the amount of p24 antigen and to thereby determine the severity with which the tissues were infected with HIV.

The assays showed that severity of HIV infection in the tissues was affected by the concentration of ranpirnase in the solution. As ranpirnase concentration increased, the level of HIV in the supernatant decreased. Hence, this experiment demonstrated that ranpirnase had a prophylactic effect on the explanted tissues; exposing the tissues to ranpirnase diminished the susceptibility of the tissues to HIV infection in a dose-dependent manner.

This experiment is strong evidence that an individual can be prophylactically protected from viral sexually transmitted diseases such as HIV by applying ranpirnase topically to body regions (e.g. genitalia, rectum, mouth) that might be exposed to HIV during sexual intercourse, prior to (or even during) sexual intercourse.

The above-referenced parent patent application discloses a topical pharmaceutical composition consisting essentially of a therapeutically effective amount of an enzymatically-active ribonuclease and a viscous vehicle that does not unacceptably interfere with the enzymatic activity, wherein the vehicle is selected from the group consisting of a gel, a serum, or a lotion. Advantageously, the ribonuclease is ranpirnase and the vehicle is K-Y® Brand Jelly.

This topical pharmaceutical composition is particularly well-suited for prophylactic application of ranpirnase (or another enzymatically-active ribonuclease) because the vehicle does not unacceptably interfere with the enzymatic activity of the ribonuclease and the viscosity of the vehicle allows the composition to remain where it has been applied so that the active pharmaceutical ingredient (e.g. ranpirnase)—does not run off.

However, it is believed that topical application of ranpirnase is not the only way to administer it for prophylactic protection. It is also believed possible to protect an individual against a virus by infecting the individual with human microbiota into which ranpirnase DNA has been transfected, or by dispensing the ranpirnase using an intravaginal ring.

Although this experiment was only carried out using ranpirnase, there is at least one other ribonuclease (identified below) that is highly homologous to ranpirnase and that has similar antiviral activities. For reasons set forth below, it is believed that any such ribonuclease will be a microbicide and will have similar prophylactic effects.

BRIEF DESCRIPTION OF THE DRAWINGS

The invention will be better understood with reference to the exemplary and non-limiting drawings, in which.

DETAILED DESCRIPTION OF PREFERRED EMBODIMENTS

Ranpirnase is a proteinaceous enzymatically-active ribonuclease having the amino acid sequence of SEQ ID NO:1, previously disclosed and claimed in U.S. Pat. No. 5,559,212.

An experiment was carried out using rectal tissue biopsies taken from six healthy HIV-uninfected volunteers. Three tissue explants were taken from each volunteer.

Five liquid mixtures were formulated to test the prophylactic effect of ranpirnase against HIV. The mixtures were $10^5$ $TCID_{50}$ of HIV-$1_{BaL}$ together with 0.06 µg/mL ranpirnase $10^5$ $TCID_{50}$ of HIV-$1_{BaL}$ together with 0.6 µg/mL ranpirnase $10^5$ $TCID_{50}$ of HIV-$1_{BaL}$ together with 6 µg/mL ranpirnase $10^5$ $TCID_{50}$ of HIV-$1_{BaL}$ together with 66 µg/mL ranpirnase together with a control:

$10^5$ $TCID_{50}$ of HIV-$1_{BaL}$ together with 0.00 µg/mL ranpirnase

The fifteen tissue explants were arranged into five groups of three, with each group of three being incubated for two hours in a single one of these mixtures (one group is incubated in the control). The tissue explants were then washed multiple times and cultured at 37° C. and 5% $CO_2$ for fourteen days, during which interval supernatant was collected on Days 3, 7, 10, and 14. The culture medium was made up of equal parts of complete RMPI and Zosyn® 50 mg/mL, with 500 mL of complete RMPI being made up of 90% RPMI 1640—445 mL, 10% Fetal Bovine Serum—50 mL, and 1% Antibiotic/Antimycotic—5.0 mL.

The severity of HIV infection of the tissue explants was determined by assaying the supernatant for HIV-1 p24 antigen using the AlphaLISA platform. The efficacy endpoint was the tissue explant weight adjusted Day 14 cumulative HIV-1 p24. As can be seen in all the Figures, increasing concentration of ranpirnase caused a dose-dependent reduction in HIV-1 p24 antigen in the tissue explants. The statistical significance p of the displayed data is shown in the Figures; whether the data are averaged or not, the results for 0.00 µg/mL, 0.06 µg/mL, and 0.6 µg/mL concentrations of ranpirnase are below the 5% level of significance. And, the results for 6.00 µg/mL and 66 µg/mL concentrations of ranpirnase are below the 1% level of significance where the results of each group of three tissue explants are averaged, and below the 0.1% level of significance where the results of each tissue explant is taken individually.

Figure 1:
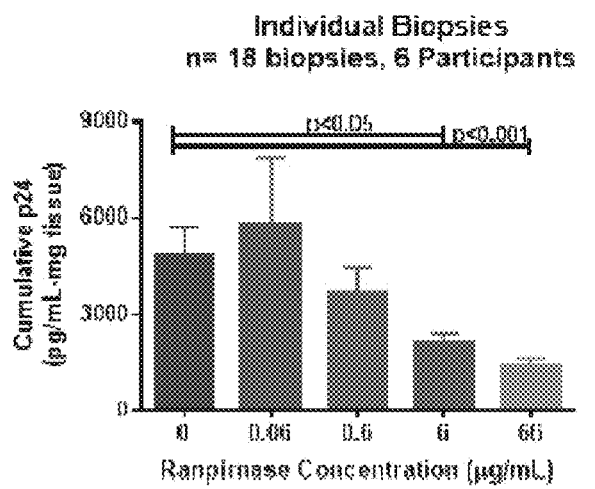
FIG. 1 graphs the cumulative HIV infection of 15 individual rectal tissue biopsies in the herein-described experiment as a function of ranpirnase concentration.
Figure 2:
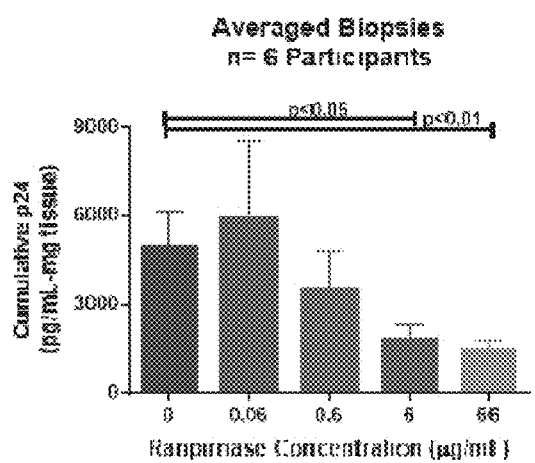
FIG. 2 graphs the cumulative averaged HIV infection of 5 rectal tissue biopsy triplets in the herein-described experiment as a function of ranpirnase concentration.
Figure 3:
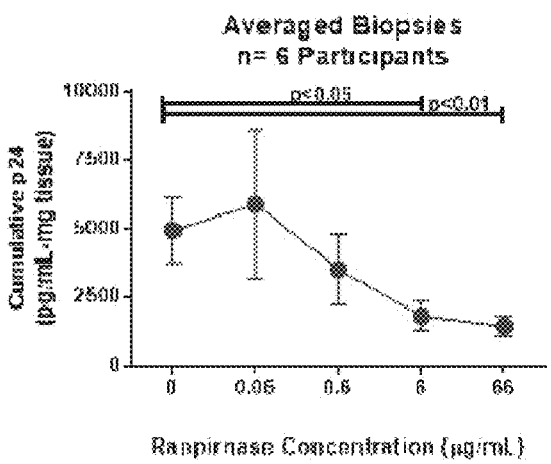
FIG. 3 graphs the data graphed in FIG. 2 in a different format to clearly show the standard error of the mean at each ranpirnase concentration.
Figure 4:
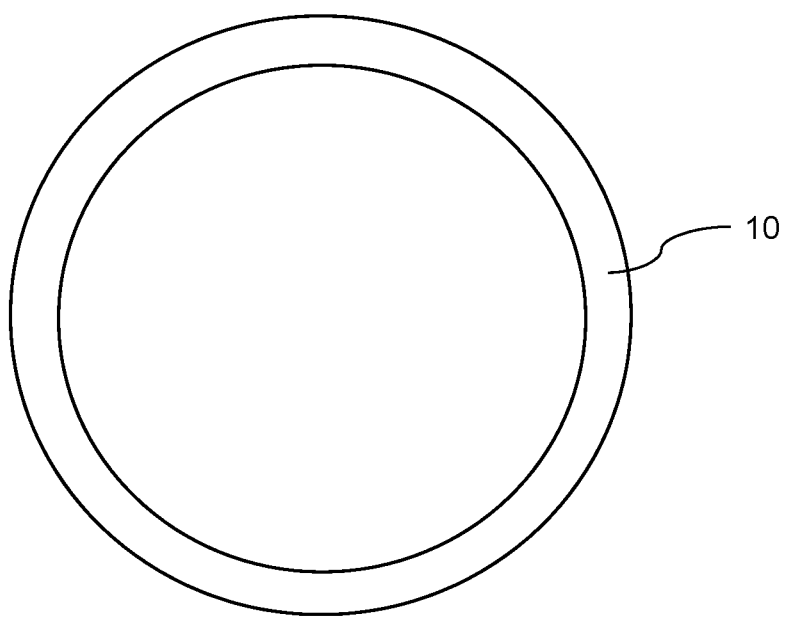
FIG. 4 shows a vaginal ring such as would be used in a third embodiment of the invention.

In each of the Figures, the standard error of the mean is also shown by the vertical lines shown by themselves in FIG. 3 and superposed on the bars in FIGS. 1 and 2. As would be expected, in instances wherein the level of significance is highly stringent (less than 1%) the standard error of the mean is smaller than in instances wherein the level of significance is less stringent (less than 5%).

It will be noted that this experiment was conducted using tissue explants from six individuals even though only five triplets of tissue explants were assayed after exposure to the identified mixtures of ranpirnase and HIV-$1_{BaL}$ and the control. This is because an additional triplet of tissue explants exposed to ranpirnase alone was subjected to an MTT assay in order to rule out the possibility that ranpirnase caused cellular toxicity.

Hence, this experiment showed that tissue explants exposed to ranpirnase—and particularly to ranpirnase concentrations of 6 µg/mL and greater—developed increased resistance to HIV infection, i.e. that ranpirnase had a microbicidal effect.

Advantageously, the topical pharmaceutical composition disclosed in the above-referenced parent patent application is used as a microbicide, and is topically applied to an individual who is to be protected. Further advantageously, the topical pharmaceutical composition can be applied to body regions that might be exposed to HIV during sexual intercourse The enzymatically-active ribonuclease can be ranpirnase. Alternatively, there is at least one other ribonuclease having enzymatic activities similar to that of ranpirnase, and this may be used instead of ranpirnase. For example, the "805 variant" (SEQ ID NO:2) is over 900 homologous to ranpirnase, in that the amino acid sequences of the two ribonucleases differ at only three positions (positions 11, 20, and 103) and has similar antiviral activities. Furthermore, it is known that the active site of ranpirnase is located at its N-terminal, and since the N-terminal amino acid sequences of ranpirnase and the ’805 variant are identical, it follows that they will encode identical active sites. Thus, a person of ordinary skill in this art would expect the ’805 variant to have the same prophylactic effect as ranpirnase has.

Although this experiment was carried out by exposing rectal tissue explants to solutions containing ranpirnase, it is believed that the same results would be achieved by using another method to deliver ranpirnase to the tissue that may be exposed to HIV. This other method, a second preferred embodiment of the invention, is by using human microbiota to produce ranpirnase. An example of this mode of administration can be found at Gebhart et al., *mBio*, Vol. 6, Issue 2, pp. 1-13, (March/April 2015). The disclosure of this publication is incorporated herein by reference.

For example, let it be assumed that mucosal tissues (e.g. the vagina, the rectum) are to be prophylactically protected from HIV. *E. coli* and *Lactobacillus* are part of the microbiota in those regions. Ranpirnase DNA can be transfected into *E. coli* or *Lactobacillus* (or both) and the thus-modified *E. coli* or *Lactobacillus* introduced into the subject. The modified *E. coli* or *Lactobacillus* would then infect the subject and thereby produce ranpirnase in the mucosal tissues involved.

Alternatively, other bacteria could be used to prophylactically protect other tissues against other viral infections. For example, probiotic *E. coli* into which ranpirnase DNA had been transfected could be used to protect against viral infections of the digestive tract. Similarly-modified saprophytic *Streptococcus* could be delivered to protect a subject’s external genitalia against HIV.

A third preferred embodiment of the invention is suitable for use by women. In this third embodiment, an intravaginal ring 10 (FIG. 4) of a suitably porous and biocompatible material (such as is described below) is impregnated with ranpirnase and inserted into the vagina, where the ranpirnase is dispensed. The ranpirnase may be mixed with other agents (e.g. dispersing agents).

Intravaginal rings are known and are used to dispense birth control drugs as well as dapivirine (a candidate microbicide now in clinical trials). An exemplary composition of such a ring is disclosed at Table 2 of Holt, et al., *Antimicrobial Agents and Chemotherapy*, Vol. 59, No. 7, pp. 3761-3770 (July, 2015), the disclosure of which is incorporated herein by reference.

Although preferred embodiments have been described above, the invention is limited only by the following

TABLE 1

| Component | Function | Amt per ring (mg) |
|---|---|---|
| Dapivirine | Active pharmacutical ingredient | 25 |
| Silicone liquid (NuSil MED-360) | Dispersing agent | 175 |
| Silicone elastomer part A (NuSil MED-4870 part A)* | | 3,900 |
| Vinyl-terminated polydimethylsiloxane (linear) polymers | Polymer | |
| Platinum | Catalyst for cross-linking reaction | |
| ~30% amorphous (noncrystalline) reinforcing silica | Filler | |
| Silicone elastomer part B (NuSil MED-4870 part B)* | | 3,900 |
| Vinyl-terminated polydimethylsiloxane (linear) polymers | Polymer | |
| Hydride functional polydimethysiloxane polymer | Cross-linker | |
| ~30% amorphous (noncrystalline) reinforcing silica | Filler | |
| Proprietary manufacturing information | Inhibitor | |

*Part A and part B refer to a two-part translucent silicone system used with injection molding equipment

We claim:

1. A method of diminishing the susceptibility of an individual to an HIV infection, comprising the step of topically applying to the individual a topical pharmaceutical composition consisting essentially of a prophylactically effective concentration of an enzymatically-active ribonuclease and a viscous vehicle that does not unacceptably interfere with the enzymatic activity, wherein the ribonuclease is ranpirnase, and wherein the pharmaceutical composition is topically applied to body regions that might be exposed to HIV during sexual intercourse.

2. The method of claim 1, wherein the ribonuclease is selected from the group consisting of ranpirnase (SEQ ID NO:1) and the '805 ranpirnase variant (SEQ ID NO:2).

* * * * *

```
                        SEQUENCE LISTING

<160> NUMBER OF SEQ ID NOS: 2

<210> SEQ ID NO 1
<211> LENGTH: 104
<212> TYPE: PRT
<213> ORGANISM: Rana pipiens

<400> SEQUENCE: 1

Glu Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
                20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
        50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
                100

<210> SEQ ID NO 2
<211> LENGTH: 104
<212> TYPE: PRT
<213> ORGANISM: Rana pipiens

<400> SEQUENCE: 2

Glu Asp Trp Leu Thr Phe Gln Lys Lys His Val Thr Asn Thr Arg Asp
1               5                   10                  15

Val Asp Cys Asn Asn Ile Met Ser Thr Asn Leu Phe His Cys Lys Asp
                20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
        50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Arg Cys
                100
```